US012654009B2

(12) United States Patent
D'Errico et al.

(10) Patent No.: US 12,654,009 B2
(45) Date of Patent: Jun. 16, 2026

(54) MEDICAL DEVICE FOR CUTANEOUS APPLICATION

(71) Applicants: Fabrizio D'Errico, Lodi (IT);
Francesco Serio, Taranto (IT);
Gianluigi Carioni, Treviglio (IT)

(72) Inventors: Fabrizio D'Errico, Lodi (IT);
Francesco Serio, Taranto (IT);
Gianluigi Carioni, Treviglio (IT)

( * ) Notice: Subject to any disclaimer, the term of this patent is extended or adjusted under 35 U.S.C. 154(b) by 275 days.

(21) Appl. No.: 18/468,923

(22) Filed: Sep. 18, 2023

(65) Prior Publication Data

US 2025/0090846 A1      Mar. 20, 2025

(51) Int. Cl.
*A61N 1/36* (2006.01)
*A61N 1/04* (2006.01)

(52) U.S. Cl.
CPC ....... *A61N 1/36021* (2013.01); *A61N 1/0492* (2013.01)

(58) Field of Classification Search
CPC .......................... A61N 1/36021; A61N 1/0492
USPC .......................................................... 607/46
See application file for complete search history.

(56) References Cited

U.S. PATENT DOCUMENTS

| | | | |
|---|---|---|---|
| 9,669,231 B1 | 6/2017 | Clark et al. | |
| 2011/0230701 A1* | 9/2011 | Simon .................. | A61N 1/0456 607/46 |
| 2014/0172062 A1* | 6/2014 | Yoon ...................... | A61N 1/205 607/149 |

FOREIGN PATENT DOCUMENTS

| | | |
|---|---|---|
| WO | 2019079291 A1 | 4/2019 |

OTHER PUBLICATIONS

Capecci, Marianna et al: "Postural Rehabilitation and Kinesio Taping for Axial Postural Disorders in Parkinson's Disease", Archives of Physical Medicine and Rehabilitation, Elsevier, Amsterdam, NL, vol. 95, No. 6, Feb. 5, 2014 (Feb. 5, 2014), pp. 1067-1075.
Conrad, O.M.; Scheidt, R.A .; Schmit, B.D. (2011) Effects of wrist tendon vibration on targeted upper-arm movements in poststroke hemiparesis. Neurorehabil. Neural Repair, 25, 61-70.
Downie, WW, Leatham PA, Rhind VM, Wright V, Branco JA, Anderson JA. (1978) Studies with pain rating scales. Ann Rheum Dis; 37: 378-381.
Garcia, L., D'Alessandro, G., Bioulac, B., Hammond, C. (2005). High-frequency stimulation in Parkinson's disease: More or less? Trends Neurosci. 28, 209-216.
Italian Search Report dated Jan. 11, 2023 from Application No. IT202200011933.
Jakobs M, Fomenko A, Lozano AM, Kiening KL. (2019). Cellular, molecular, and clinical mechanisms of action of deep brain stimulation—a systematic review on established indications and outlook on future developments. EMBO Mol Med. Apr. 11.
Lee, G., Cho, Y., Beom, J., Chun, C., Kim, C. H., & Oh, B. M. (2014). Evaluating the differential electrophysiological effects of the focal vibrator on the tendon and muscle belly in healthy people. Annals of Rehabilitation Medicine, 38(4), 494-505.
Macefield et al., "Functional properties of human muscle spindles", J Neurophysiol 120: 452-467, 2018.

(Continued)

*Primary Examiner* — Nadia A Mahmood
(74) *Attorney, Agent, or Firm* — INNOVATION CAPITAL LAW GROUP, LLP; Vic Lin

(57) ABSTRACT

The present invention relates to a medical device for cutaneous application. Such medical device is characterized by a multilayer configuration and comprises an insulating layer having a specific dielectric constant.

22 Claims, 4 Drawing Sheets

Dendrites
Nucleus and nucleolus
Soma
Myelin sheath
Axon
Node of Ranvier
Synaptic buttons

(56) References Cited

OTHER PUBLICATIONS

Marconi, B.; Filippi, G.M.; Koch, G.; Giacobbe, V.; Pecchioli, C.; Versace, V.; Camerota, F.; Saraceni, V.M.; Caltagirone, C. (2011) Long-term effects on cortical excitability and motor recovery induced by repeated muscle vibration in chronic stroke patients. Neurorehabil. Neural Repair, 25, 48-60.

Michener et al., "Responsiveness of the Numeric Pain Rating Scale in Patients With Shoulder Pain and the Effect of Surgical Status", Journal of Sport Rehabilitation, 2011, 20, 115-128.

Noma, T.; Matsumoto, S.; 49 Shimodozono, M.; Etoh, S.; Kawahira, K. (2012) Anti-spastic effects of the direct application of vibratory stimuli to the spastic muscles of hemiplegic limbs in post-stroke patients: A proof-of-principle study. J. Rehabil. Med., 44, 325-330.

Oyeka, D.O. et al: "RFID sticking plasters", Antennas and Propagation Conference (LAPC), 2012 Loughborough, IEEE, Nov. 12, 2012 (Nov. 12, 2012), pp. 1-4.

Paoloni, M.; Mangone, M.; Scettri, P.; Procaccianti, R.; Cometa, A.; Santilli, V. (2010) Segmental muscle vibration improves walking in chronic stroke patients with foot drop: A randomized controlled trial. Neurorehabil. Neural Repair, 24, 254-262.

Paoloni, M.; Tavernese, E.; Fini, M.; Sale, P.; Franceschini, M.; Santilli, V.; Mangone, M. (2014) Segmental muscle vibration modifies muscle activation during reaching in chronic stroke: A pilot study. Neuro Rehabilitation, 35, 405-414.

Pei, Rui et al: "Wearable antenna design for bioinformation", 2016 IEEE Conference on Computational Intelligence in Bioinformatics and Computational Biology (CIBCB), IEEE, Oct. 5, 2016 (Oct. 5, 2016), pp. 1-4.

Ribot-Ciscar, E., Roll, J. P., & Gilhodes, J. C. (1996). Human motor unit activity during post-vibratory and imitative voluntary muscle contractions. Brain research, 716(1-2), 84-90.

Vallbo AB, Hagbarth KE, Torebjork H, Wallin BG (1979) Somatosensory, proprioceptive and sympathetic activity in human peripheral nerves. Physiol Rev 59:919-957.

* cited by examiner

MEDICAL DEVICE FOR CUTANEOUS APPLICATION

FIELD OF THE INVENTION

The present invention relates to a medical device for cutaneous application. Such medical device is characterized by a multilayer configuration and comprises an insulating layer having a specific dielectric constant.

BACKGROUND

From the anatomical point of view, the nervous system which in the postural and dynamic field operates, adjusts, and controls the muscle tone and the complex actions of contractions and relaxations of the antagonists is composed by a central nervous system (also referred to as SNC below) and a peripheral nervous system (also referred to as SNP below). In the same manner, the sensory collection of the stimuli, the cognitive processing, transmission, and transduction thereof which operates for perceiving and modulating the pain is developed both at a level of SNP and SNC.

SNC comprises the brain (i.e., brain hemispheres, diencephalon, cerebellum, and brain stem) and the spinal cord. The SNP comprises the sensory neurons (cells specialized in transducing the stimuli in nerve impulses and their transmission, see FIG. 1) which connect the sensory receptors disposed on the surface of the body, or more deeply therein, with the corresponding processing circuits in the SNC. With a general overall picture, the stimuli from the external environment are locally processed in signals (transduction), the latter transmitted as an assembly of information to the processing circuits located in the brain and/or the spinal cord (afference) which in turn interpret the meaning thereof (processing) and send signals to the peripheral effectors (efference) as a thoughtful response to the stimulus.

In particular:
- a. in the proprioceptive field, namely in relation to the complexity of evens regarding the sense of position and the movement of the limbs and the body both in static (posture) and dynamic phase (movement) the muscle-origin retroaction signal—the so-called proprioceptive feedback—underlies two main types of mechanisms: those involved in local reflex adjustment and motor assistance and those which, through the transmission of the signals transduced based on the local stimulus, convey the parameters of various motor activities towards the central nervous system (SNC), allowing the processing thereof both at a conscious and unconscious levels [1-4];
- b. in the nociceptive field, namely in relation to the complexity of neurophysiological and neurochemical events related to the physiological pain sensitivity which occur below the thalamus, following the activation of the nociceptors, the information in the form of signal is sent to the SNC for the conscious sensory effect. Actually, in the context concerning the present discussion in the field of pain, the synthesis should be completed also considering the neuropathic pain, namely the type of pain whose perception does not depend on algogenic stimuli which interest the peripheral receptors (somatic or visceral) as in the case of the nociceptive pain; the neuropathic pain is indeed reconducted to an intrinsic lesion of the nerve pathway, followed by alterations in receiving or transmitting the pain message (peripheral, peripheral-central and central).

In extreme synthesis, some details are below. The processing carried out by the nervous system allows to pass from the feeling, i.e., the pure and simple recording of the sensory stimulus (for example of the pain type—nociception—or related to the sense of position and movement of the limbs and the body—proprioception) to the perception, i.e., an interpretation of the received message. However, for the benefit of the synthesis picture regarding the application field of the present invention, referring to those peripheral and local organs which perform the primary phase of collecting information based on the received stimuli and overall determine the sensitivity of the human body in response to complexity of the stimulations provided by the environment is essential. These peripheral elements are the receptors, those specific cells able to receive signals and to react to the different stimuli. Five main types of receptors are distinguished: a) thermoreceptors, sensitive to temperature, which transmit the feelings of hot and cold; b) nociceptors, sensitive to pain; c) mechanoreceptors, sensitive to different types of pressure; d) chemoreceptors, sensitive to the presence of specific chemicals; e) electromagnetic receptors, sensitive to the energy related to phenomena such as electricity or magnetism. For example: in adjusting the muscle tone, most of the central neurons appointed to such function are motoneurons which are able to adjust the activity of the muscles to which they are connected. Motoneurons are the efferent neurons (i.e., those transporting the signal towards the SNP) of these circuits: a group of motoneurons sends the effector signal to the flexor muscles of the limb, while another sends it to the extensor muscles. However, a suitable modulation of these efferent signals which travel towards the extensor and flexor muscles should be set for a correct movement of the limb. Such modulation in ensured by the third key element of the nerve circuit consisting of interneurons of the ventral horns of the spinal cord. Indeed, interneurons receive the signals through the synaptic contacts from the afferent sensory neurons, set the synapses with the efferent motoneurons and are capable of modulating the input and output signals: if on one hand the motor synaptic (excitatory) connections between the sensory afferent neurons and the efferent neurons which are directed to the extensor muscles are maintained, causing the contraction of the flexor muscle, on the other hand, and simultaneously, the synaptic connections between the afferent neurons of the extensor muscle are of the inhibitory type and therefore activating them reduces the electric activity of the efferent motoneurons of the extensor muscle which therefore remains stretched not contracting. The result is an activation of the agonist (flexor) muscles and a simultaneous inactivation of the antagonist (extensor) muscles which control the position of the leg (see FIG. 2).

The signal is locally transduced from the received stimuli and transported by the neurons inside the nerve circuit (afferent and efferent) is an electric-type signal which more precisely is generated by electrochemical reactions. Neurons are not in themselves good electricity conductors, as for example a copper wire is, which notoriously is an excellent electricity conductor, i.e., able to flow the negative free charges, i.e., the free electrons of the metal binding, therein. In contrast, neurons have propagative electrochemical mechanisms able to generate the flow electric signals along the nerve fibre of the neuron or axon. Such mechanisms are based on the passage of ions through the cytoplasm membrane of the neurons, as summarized below:

Between the extracellular and the intracellular zones, a different concentration of these ions, primarily $Na+$ ions which maintain a greater concentration in the extracellular fluid than the membrane intracellular zone, is made;

This asymmetrical distribution of ions between extracellular and intracellular zones of the plasma membrane produces by electrochemical gradient a difference in electric potential of the membrane called membrane resting potential equal to about −70 mV.

The ion concentration gradients are maintained constant by proteins known as active transporters which, as suggested by their name, actively move ions inside or outside the cells moving them in a direction opposed to their concentration gradients.

The plasma membrane of a neuron is selectively permeable to some ions in the extra- and intracellular fluid, primarily Na+ and K+; this selective permeability is mostly due to the presence of ion channels, namely proteins which allow only certain types of ions to pass through the membrane in the direction of their concentration gradients. In balance conditions the cell membrane of the neurons results polarized as it exhibits a difference in electric charge between the inside and outside of the cell. The resting potential is maintained by the action of the membrane protein transporting the Na+ and K+ ions (called sodium-potassium pump) which (actively) transports Na+ ions from the inside to the outside of the cell and K+ potassium ions from the outside towards the inside, thus moving such ions against their concentration gradient. On the other hand, K+ ions can freely pass through membrane proteins (also called ion channels for potassium) and tend to balance their concentration, moving from the outside to the inside. Actually, Na+ ions would be also evenly distributed passing through other channel proteins for sodium (also called ion channels for sodium), but this does not occur because when the neuron is resting, these channels are closed and prevent to cancel the existing concentration gradient between the membrane extracellular zone and intracellular zone. A resting ion concentration potential (electrochemical potential) being maintained constant around the value of about −70 mV (see again FIG. 3) is determined on the basis of this electrochemical mechanism. In extreme synthesis, the resting membrane potential, negative towards the inside, is the result of a clear outflow of K ions through the neuronal membranes which are mostly permeable to K.

The ion channels can perform their own function of selectively allowing the passage of the main Na+ and K+ ions obviously when open to put in direct communication the extracellular fluid with the intracellular fluid at different ion concentration. Such channels are distinguished between:

passive ion channels, always open;
mechanically-adjusted ion channels;
chemically-adjusted ion channels;
voltage-dependent ion channels.

The result of this clear flow of sodium ions is a progressive increase of the membrane potential from the resting value of −70 mV to less negative values. If the membrane potential of the afferent neuron reaches a value equal to about −50 mV, many voltage-dependent channels for sodium open and a large number of Na+ ions pass from the outside to the inside of the cell. This potential which triggers the opening of the sodium channels is called threshold potential. The positive charge concentration of the intracellular zone increases due to the migration of Na+ in the intracellular fluid. The membrane potential, finally, is suddenly inverted and reaches a value of +35 mV, which is called action potential. This sequence of events known in literature is called depolarization of the membrane. However, a few moments after reaching the action potential the channel proteins for sodium are closed again, while those for potassium—which meanwhile were closed—are opened again. Because of the action of the sodium-potassium pump, the conditions of the resting membrane are finally reset. This last phase of the process is called repolarization of the membrane.

The action potentials propagate throughout the length of the axons and transfer information from one point to the other inside the nervous system. Actually, the nerve impulse, the electric signal running along the nerve fibre, is generated by the sudden change of the membrane potential. The axons (see again FIG. 1) can transport electric signals along long distances because of the self-regenerating electric activity wave formed by the action potential. The action potentials are also called "spikes", "discharges" or "unitary responses" because they actually consist of an "all or nothing" variation of the electric potential of the membrane of the neuron. Finally, both the sensory neurons and the neurons which perform the function of processing and integrating, transmit the impulse to other nerve cells. Motor neurons, instead, pass the stimulus to the muscular cells. The nerve impulse is transferred from one cell to the other and to the muscular cells through the synapses, namely the contact points between two neurons or between a neuron and a muscular cell which transmit the nerve impulse arrived at the end of the axon propagated from the action potential to the next cell. Finally, both the sensory neurons and the neurons which perform the function of processing and integrating, transmit the impulse to other nerve cells. Motor neurons, instead, pass the stimulus to the muscular cells. The nerve impulse is transferred from one cell to the other and to the muscular cells through the synapses, namely the contact point between two neurons or between a neuron and a muscular cell which transmit the nerve impulse arrived at the end of the axon propagated from the action potential to the next cell.

Action Potentials and Perception of Pain

The pain can be classified as nociceptive, when there is a direct activation of the receptors of the nociception, neuropathic when the central and/or peripheral nervous systems are interested, psychic and mixed. The nociceptive nerve endings are formed by specialized receptors which are able to transform the energy associated with mechanical, thermal, or chemical stimuli in a variation of the membrane potential, making the action potentials due to the activity of the voltage-dependent sodium channels. In the form of wave "trains", the action potentials proceed through ways afferent to SNC. When the depolarization of the nociceptors is caused by a tissue peripheral lesion, the resulting production of the action potential is able to locally cause the release of neuropeptides from the same nociceptive endings which locally causes the degranulation of mastocytes, stimulating the inflammatory process through chemical mediators such as histamine. The presence of histamine is able in turn to activate, in cycle, the same nociceptive endings which will therefore increase the emission frequency of the action potentials and the resulting transmission of the afferent nociceptive signal. When the nociceptors are exposed to cyclic or permanent stimuli (long period) an enhancement of the response to the harmful stimuli is produced, a phenomenon known as sensibilization. The nociceptors become more sensitive (thus excitable) by the inflammation mediators with widening of the response to the painful stimulus (hyperalgesia and allodynia). In such case, the emission of low-frequency action potentials persists for several days. This, indeed, is one of the mechanisms underlying the chronic pain. The action potentials and their generating electrochemical mechanism (i.e., the voltage-dependent sodium and potassium channels) are actually the target of many drugs, including anaesthetics. When treating pain, local anaesthetics such as lidocaine and procaine operate preventing the action potentials from propagating along the peripheral nerves obstructing the passage of Na+ through the sodium ion channels, despite being in the open configuration.

Posture and Action Potentials of Motoneurons

The efferent circuits descending from the upper motoneurons, together with the inter-segment circuits of the spinal cord, are appointed to control the posture and to adjust the musculoskeletal movement. Motoneurons—or motoneurons α—are long neurons which, by innervating the fibres of the striated muscle, are responsible of the impulses acting on the flexor and extensor striated muscles for maintaining the posture and developing the movement. Together with motoneurons, there are also small motoneurons which innervate specialized muscle fibres, the muscle spindle. These small motoneurons—or motoneurons γ —are actually the sensory receptors which, placed parallel to the fibres of the striated muscle, have the function of adjusting the force, namely the contraction of the flexor muscles and the relaxation of the extensor muscles. The neuromuscular spindles are contained inside connective tissue capsules (thus they are also called intra-spindle), in contrast to the non-encapsulated surrounding fibres of the striated muscle (or extra-spindle). The sensory axons which send the information on the length of the muscle directly to the spinal cord and the brain stem directly innervate the intra-spindle muscle fibres. The function of motoneurons γ is thus to control the sensory transduction in order to dynamically adjust—moment by moment—the length of the intra-spindle muscle fibres at a suitable length. Actually, in adjusting the maximum reaction force of the muscle (i.e., performing the contraction) another sensory receptor, the Golgi tendon organ, consisting of encapsulated afferent nerve endings which are at the connection of the muscle to the tendon and disposed in series with the latter, intervenes. Both in the case of intra-spindle motoneurons disposed parallel to the muscle fibre and in the case of the Golgi tendon organs disposed in series on the muscle-tendon connection, when a muscle is actively contracted the produced force acts respectively on the intra-spindle fibres and on the tendon, causing an increase in the tension of the cell membrane of the motoneuron γ or the collagen of the tendon organ in the case of the Golgi organ and the resulting compression of the sensory endings. After the mechanical stimulus, the resulting deformation of the cell membrane of the motoneurons specialized in controlling the muscle tone activates the mechano-sensitive cation channels present in the sensory endings generating a potential which, if above the threshold, is able to trigger the generation of action potential trains which propagate along the axons of the afferent circuits. Axons from the motoneurons of the Golgi organ set synapses with interneurons inhibiting the spinal cord which in turn set synapses with the motoneurons α which innervate the same muscle. This reflected circuit also operates at lower muscle force levels, neutralizing the effects of small changes in muscle tension by increasing or inhibiting the motoneurons α. The same afferences also set synapses with exciter local interneurons which increase the excitability of the motoneurons α which innervate the antagonist muscle. Thus, for force levels lower than the critical threshold, the Golgi tendon organ actively contributes as a controller of the tension stationary level for a given articular angle, contrasting the effects which would reduce the muscle force (e.g., fatigue). For completing the picture known nowadays, both the neuromuscular spindle circuit and the Golgi tendon organ system can be considered open stimulus and action circuits: i.e., the inhibitory interneurons can receive synaptic stimuli from various other sources, including the external receptors, the cutaneous receptors which detect touch, pressure, variations of temperature, painful stimuli. All this premised, for the purpose of the present disclosure on the state of the known art, it is essential to refer to what occurs at the level of generating and transducing the stimulus in motoneurons. Again, reference should be made to the mechanism of the action potentials and, particularly in the postural field, at their emission and transmission frequencies. The increase of propagation and emission frequency of the action potential is due to the time summation of muscle contractions which appear in quick succession. The muscle fibres are activated by the next action potential before completing their relaxation and the forces developed by these time-overlapping contractions are thus summed. For example, the lowermost discharge frequencies recorded during a voluntary movement are in the order of 8 Hz. Upon increasing the discharge frequency of the single motor units—up to a maximum of about 20-25 Hz—the produced force increases. Recently, it has been suggested that in some muscles, the proprioceptive feedback could have an adjusting function in controlling the posture, and an assisting function in others [5]. For example, the vibrational stimulation by means of cyclic pressure waves applied on the ankle has been demonstrated to induce a postural swing in the direction of the vibrated side, indicating a reflected adjustment while a subject tried to compensate the simulated elongation of the vibrated muscle. Conducted studies show post-vibration motor and kinaesthetic effects [6]. In summary, the sensory discharge induced by the vibrations as a pressure external stimulus produces powerful prolonged effects on the motor system at a postural level. The specialized literature dealing with the improvement of the proprioceptive response following a therapeutic treatment with Local Mechanical Vibration, otherwise known with the acronym FMV (Focal Muscle Vibration) starting from 1963 describes the external stimulation with low-width tissue vibration and with a controlled frequency is able to stimulate some types of nerve receptors used in the motor control improving the posture, intervening with beneficial effects of improving the motor and postural performance, in recovering in rehabilitation treatments and in improving the movement in patients affected by serious degenerative neuropathies.

Possible Relations Between the Inhibition of the Action Potentials in the Afferent Axons in the Non-Pharmacoloqical Therapy of Parkinson's Disease Parkinson's disease is a neurodegenerative process mainly consisting of the progressive degeneration of dopaminergic neurons located in the substantia nigra of the midbrain which underlie the production of dopamine. Dopamine intervenes in the neuronal circuit, also called nigro-striatal, essential in integrating to each other the activities of perception, storage, learning and motor execution. Despite the still existing doubts about the action mechanism thereof, the stimulation of the deep part of the brain or DBS (Deep Brain Stimulation) gave hope to thousands of patients suffering from neurological disfunctions such as the late-stage Parkinson's disease and which therefore do not find benefits of the pharmacological treatment mainly based on correcting dopamine deficit [7] anymore. As an invasive therapy, but less destructive than ablative stereotactic surgery, BDS consists in implanting two electrodes up to the components of the ganglia of the base and the thalamus located deeply in the prosencephalon. The electrodes are thus connecting to an internal impulse generator. The settings of the stimulator can be telemetrically adjusted. Still object of studies, the mechanisms by which DBS creates benefit are not fully known. The stimulating variables used in DBS in patients are likely to activate large axons. Activating high-frequency large axons could inhibit a nucleus by pre-synaptic release of inhibitory transmitters. A stimulation at different degrees of intensity of the deep part of the brain can induce a local release of neurotransmitters and neuromodulators. It can also lead to the generation of action potentials in the afferent axons, in the cell bodies of the neurons, in the efferent axons and in the "passing fibres" which originate in other sites. The block of the depolarization of the neuronal membrane, the generation of action potentials, the release of neurotransmitters are possible mechanisms to explain the therapeutical effects of DBS in Parkinson's disease [8]. In particular, the effects of the electric stimulation on some intrinsic properties of the membrane, as the voltage-dependent ionic conductances, can block the production of action potentials, thereby making the hit neurons silent. Ideally, the effect of these different changes would consist in improving the anomalous network activity which affects the normal activity of the upper motoneurons.

For the non-invasive therapeutical treatment of pathologies and conditions illustrated above, devices producing cyclic pressure stimulations both supplied by external source and wearable, with supply by batteries or similar whose action is based on transmitting vibrational energy to muscle tissues able to improve the proprioceptive response, are known. The specialized literature which, starting from 1963, deals with the beneficial effects of the improvement of the proprioceptive response based on the transmission of vibrational energy focused on target tissues defines this treatment methodology by the name Local Mechanical Vibration, otherwise known with the acronym FMV (Focal Muscle Vibration). It is known that low-width vibrational external stimuli with a controlled frequency which are transmitted to the tissues are able to stimulate some types of nerve receptors used in the motor control improving the posture, intervening with beneficial effects of improving the recovery performance in rehabilitation treatments and in improving the movement in patients affected by serious degenerative neuropathies [9-14]. The sustained sensory discharge induced by the vibration produces powerful prolonged effects on the motor system at a postural level. Despite the action mechanism of the FMV in the therapeutic treatment has not been completely clarified yet, it is assumed to be based on the post-effects of the long-term consequences of the motor actions. Several studies assumed the mechanism of increasing the frequency of the action potential of the afferent fibres due to the activation of the muscle spindles via FMV. For FMV applied to lower limb muscles, such as quadriceps during the resting phase of deambulation, the afferent discharges of group "la" also contributed to trigger the locomotor phase [9]. Some studies assume that the beneficial effects of FMV could depend on the inhibitory/excitatory state inside the motor system reflecting the lesion site for patients with ictus [11].

Devices wearable contacting the cutis, not supplied by external source which, based on thermal effect based on quantity of heat transferred from the cutis to the device, self-produces a mechanical focal micro-vibration with a non-constant frequency of about 9000 Hz (above the range 100-300 Hz considering standard frequencies for a proprioceptive stimulation) and with very low-pressure levels comprised around values of about 3-4 $10^{-6}$ Pa, are further known.

Patent Applications WO 2019079291 A1 and U.S. Pat. No. 9,669,231 B1 are also part of the prior art.

In particular, International Patent Application WO 2019079291 A1 describes an active-type device wherein an active substance/agent is released. In particular, it concerns a transdermal delivery device, i.e., an active layer having a coating for releasing, when contacting the epidermis, a general drug/cosmetic released in a quantity "therapeutically/cosmetically effective of an active agent dispersed in the polymer matrix". Therefore, the device (medical in case of delivering a drug) described in Application WO 2019079291 A1 is of the active type, intended to administer in the organism and/or to subtract from the organism medicines, body fluids or other substances. Such a device, if placed on the market, would be classified as an active medical device of the IIa type, as classified according to EU Regulation 2017/745.

U.S. Patent Application U.S. Pat. No. 9,669,231 B1, instead, relates to a device which locally develops heat because of an electromagnetic field emitted by an antenna connected to an output of the medical appliance, including a signal generator, a two-direction coupler, and a controller. Such a device, if placed on the market, would be classified as an active medical device of the IIb type, as classified according to EU Regulation 2017/745.

Based on the above, both the devices described in the mentioned Patent Applications are of the active type, requiring a supply, and/or adapted to release/administer in the organism and/or to subtract from the organism medicines, body fluids or other substances.

For the treatment of the above-described pathologies, in order to maximally simplify and accordingly to reduce costs for the public in comparison with the above-mentioned devices, there is the need to find an alternative medical device wearable contacting the cutis, not being supplied by any external energy source, which maintains its (intrinsic) physical-chemical properties unaltered (thus persisting the therapeutical action over time), without using any type of vibrational energy in its action.

BRIEF DESCRIPTION OF THE INVENTION

The Applicant has now found a new multilayer medical device for cutaneous application, comprising an electrically insulating layer having a specific dielectric constant. Such medical device is therapeutically effective in treating nervous system diseases, algodystrophy syndromes, imbalance due to postural alteration and neurological syndromes or combinations thereof.

Therefore, in a first aspect, the present invention relates to a medical device as reported in claim 1.

An advantage of the medical device object of the present invention is the easy and practical cutaneous application in the one or more involved areas (topic use), for example areas detected by specific mappings for application on the target zones for therapeutical action. Advantageously, the medical device of the invention is not supplied by any external source, for example batteries. Such medical device is wearable and is easily appliable at cutaneous level in specific-interest areas. The medical device according to the invention is able to intervene directly on the physiological mechanisms underlying the activity of the voltage-dependent ion channels. Indeed, the device of the invention is able to interact with the voltage-dependent ion channels of the membrane of the afferent circuits located in the target application points. Without relating to any theory, the functional substrate contacting the cutis, because of its polarization induced by the electrochemical internal activity of the target receptors, is assumed to be able to interact with the activity of the membrane voltage-dependent ion channels of the afferent neuronal circuits, intervening in reducing the action potentials and their emission frequency in the form of wave trains of action potentials. Another advantage is related to the duration over time of the functionality of the medical device which therefore maintains an activity of the functional layer over time and does not have problems of "loss of properties".

Further aspects, embodiments, features, and advantages will result from the embodiments reported in the following description, even in the form of an example.

Furthermore, the invention is also described in the claims, whose definitions are an integral part of the present description.

DETAILED DESCRIPTION OF THE INVENTION

Figure 1:
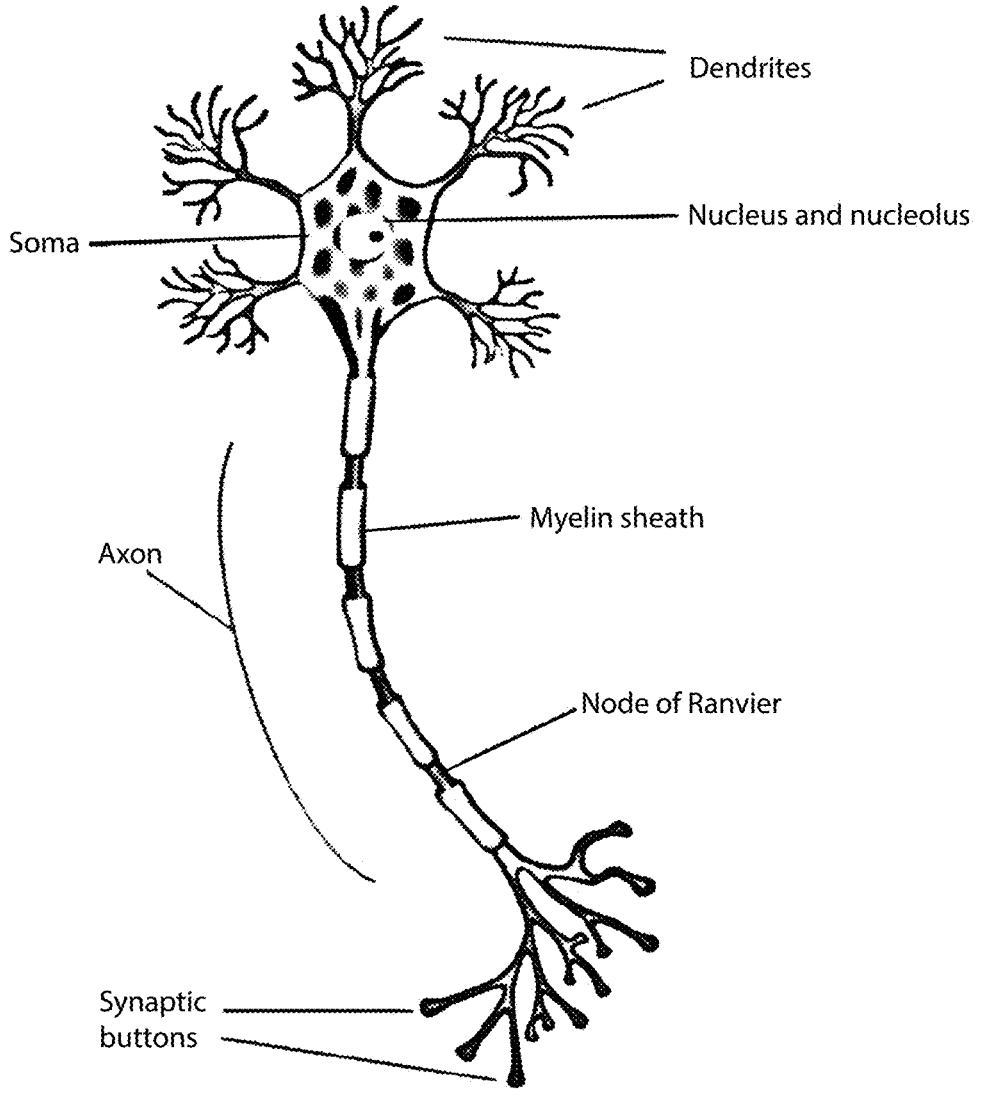
FIG. 1: representation of a neuron, highly-specialized basic cell of the nervous system which, based on the specific physiological and chemical properties, is able to receive and transmit signals—nerve impulses—through synapses. The central part of the neuron is called soma, and consists of the pyrenophore, where the nucleus is located, and other organelles. Cytoplasmatic prolongations, called neurites, originate from the cell body, which are the dendrites and the axon: the dendrites: receive signals from the other cells in the direction of the pyrenophore, are less efficient conductors; the axon: sends the signal to other cells, is an excellent conductor because of myelin.
Figure 2:
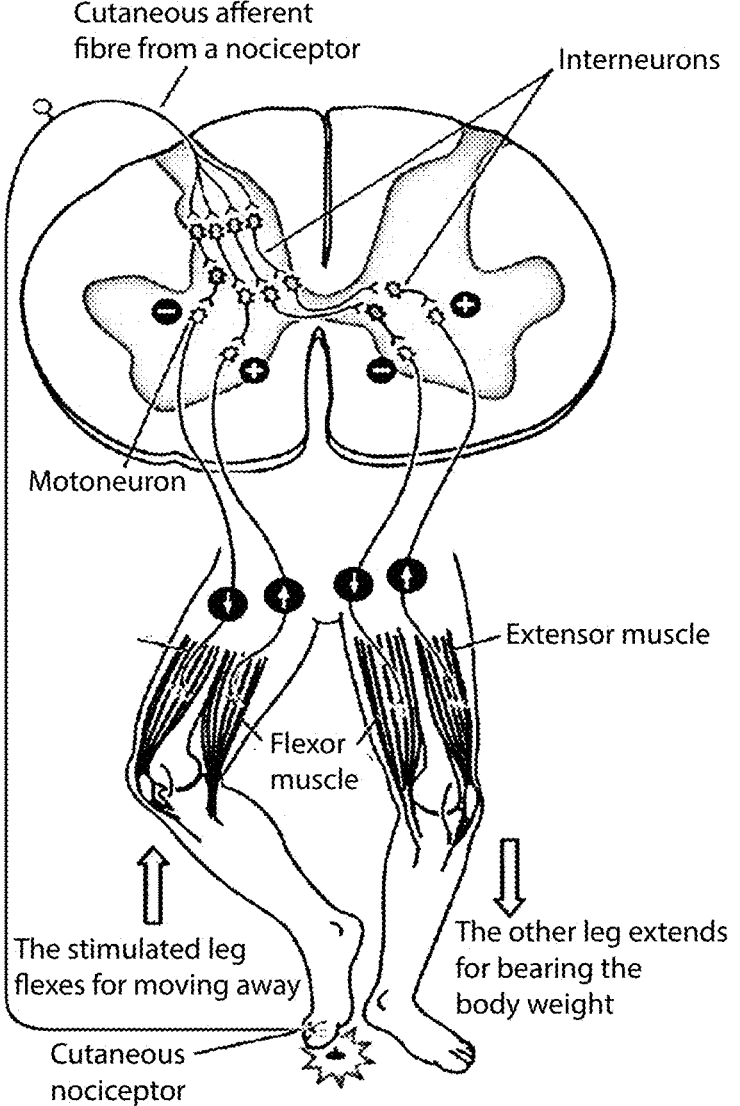
FIG. 2: exemplification of the nerve circuits responsible of the crossed extension—flexion reflect. Stimulating cutaneous receptors able to detect a tissue damage (nociceptors) of the foot caused by stepping on a sharp object determines the activation or local circuits of the spinal cord (the interneurons) which, with their synaptic responses and connections, modulate the efferent signals of the motoneurons causing: activation of the efferent signals for retracting (flexing) the stimulated end and inhibiting the efferent signals along the motoneurons which maintain the contralateral limb in extension, all for coordinating the compensatory reflected movement.
Figure 3:
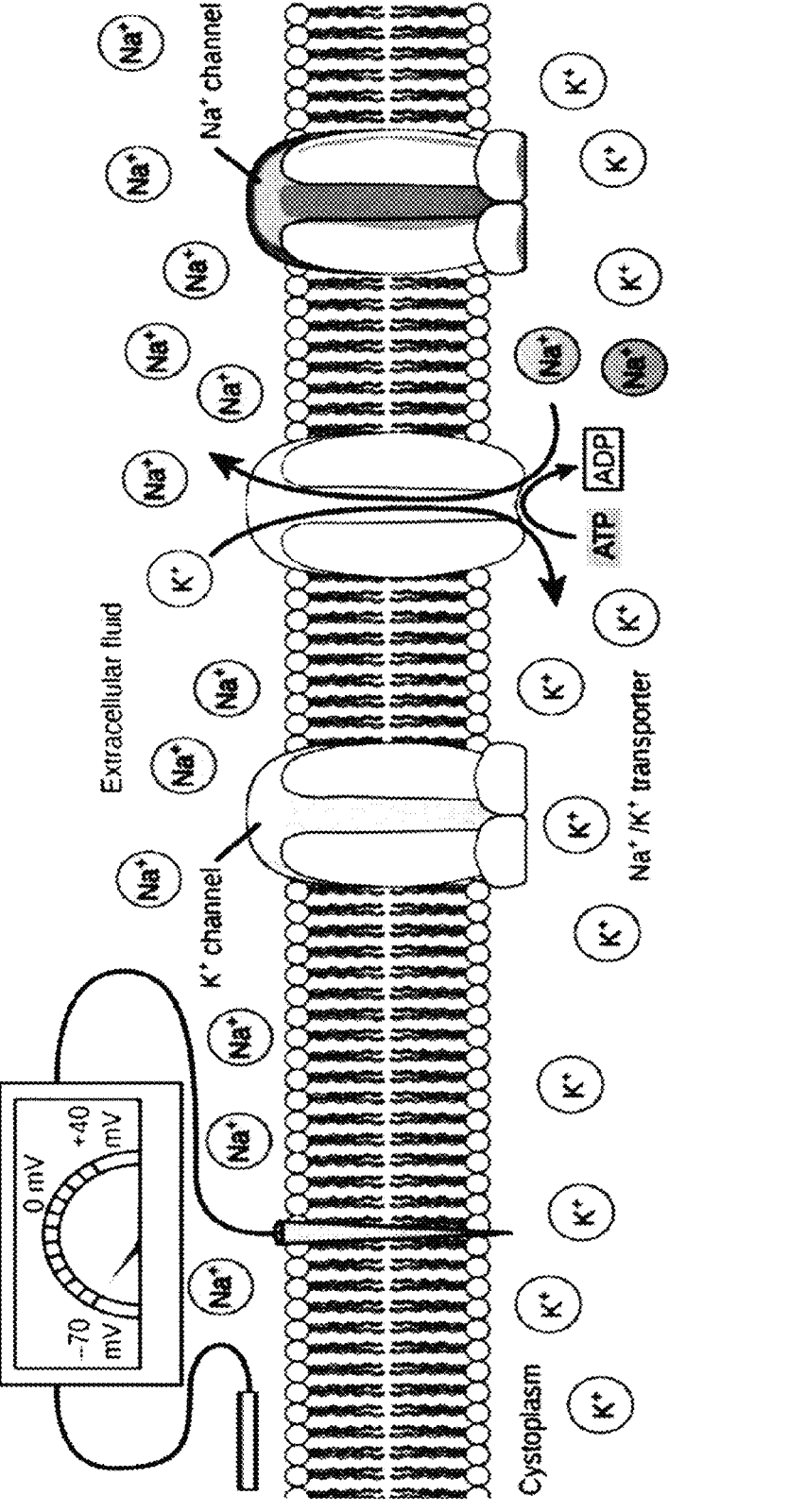
FIG. 3: scheme of the electrochemical phenomenon which makes the membrane potential of the neuron in resting conditions, namely no signal transmitted by the neuron; in figure, the cell membrane with different ion concentration in the extracellular and intracellular fluid zones is shown. The polarization of the membrane is schematically depicted from the applied electrode to the voltmeter on the left in the figure which measures at rest about −70 mV. This difference in potential between the inside and outside of the cell membrane of the neuron depends on the electrochemical actions carried out by the main ion transport elements through the membrane, namely: a) ion channels selectively permeable to potassium (in figure "K+ channel"), b) ion channels selectively permeable to potassium ions (in figure "Na+ channel"), c) charge transporters which move sodium and potassium ions in opposition to their gradient.
Figure 4:
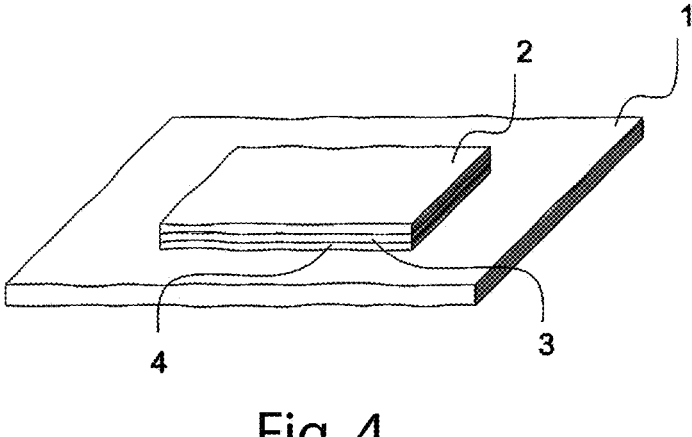
FIG. 4: perspective view of a preferred, but non-limiting, embodiment of the multilayer medical device of the invention intervening in modulating and reducing the emission of the action potentials by the receptors distributed in the epidermis and in the dermis of the application target zones in order to improve the performance of the posture, the control of the movements of patients affected by episodic or chronic diseases connectable to disfunctions of the ion channels.
Figure 5:
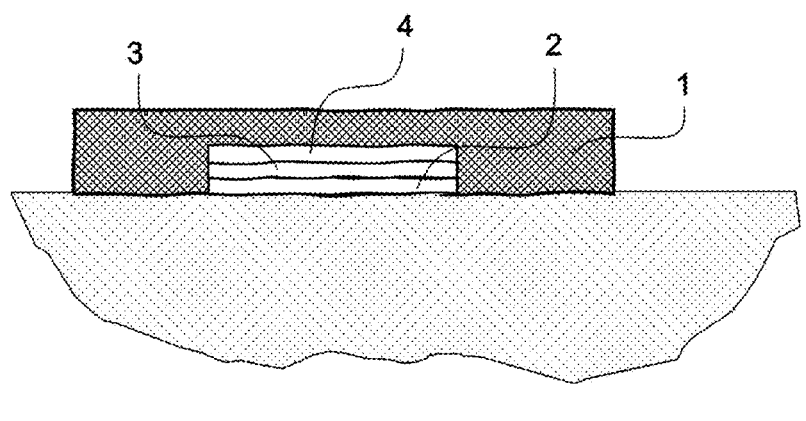
FIG. 5: cross-sectional view of said device which describes a possible and preferred embodiment of the present invention.

For the purposes of the invention, the definitions of some terms used in the present description and in the attached claims are provided below.

In the present text, the term medical device is intended to include a patch.

Accordingly, the expression medical device for topic use includes any application which actually provides the application of said device on the skin or cutis.

In the present text, the expression "functional insulating layer" (simply "functional layer"), also identifiable by reference number (2), means an active-action layer for therapeutical purposes reported herein.

In the present text, the term support layer, also identifiable by reference number (1), means the most external layer, whose inner surface, when the medical device is applied to the cutis, is oriented towards the cutis itself.

Therefore, according to a first aspect, the invention relates to a multilayer medical device for cutaneous application comprising:

a support layer (1);

a functional insulating layer (2) having a relative dielectric constant, at 1 MHz, from 2.0 to 5.0.

In a preferred embodiment, said medical device is not supplied by any external energy source.

Thereby, the medical device according to the present invention is not active, since it is not supplied by any internal or external energy source and not able, or intended, to provide or exchange energy with the human body. Furthermore, said medical device is inert and thus hypoallergenic because it does not release any administration in the organism and/or to subtract from the organism medicines, body fluids or any other substance.

It should be considered that said medical device according to the invention, if placed on the market, would be classified as a non-active non-invasive device of class I, according to the second EU Regulation 2017/745. Preferably, with reference to the functional insulating layer (2), the relative dielectric constant, at 1 MHz, is from 2.0 to 4.0, more preferably from 3.0 to 4.0.

Preferably, the dielectric constant can be defined as a relative dielectric constant according to the DIN 53483-1 standard at 1 MHz. As known to the skilled person, the measurement of the dielectric constant can be also carried out at other frequencies and therefore the result will accordingly vary.

According to a preferred aspect, the functional insulating layer has a dissipation factor, at 1 MHz, lower than or equal to 0.05.

According to a further preferred aspect, the insulating layer has a thermal conductivity W/(K*m) lower than or equal to 0.29.

According to a further preferred aspect, the functional insulating layer (2) has a surface comprised between 2 and 12 cm², preferably between 4 and 10 cm², even more preferably between 5 and 9 cm². According to a particularly preferred aspect, the functional insulating layer (2) has a surface comprised between 6 and 8 $cm^2$.

As for the functional insulating layer (2), it preferably comprises at least one polymer. Said at least one polymer is preferably a polyester.

According to a preferred embodiment, said functional insulating layer (2) is a polymeric layer. Preferably, said polymeric layer comprises a polyester.

Preferably, said polymeric layer consists of one or more polyesters.

According to a preferred aspect, the polyester is selected from polybutylene terephthalate (PBT), polycarbonate (PC), polyethylene terephthalate (PET), poli (propylene terephthalate) (PTT or PPT), poli(butylene succinate) (PBS), poli (ethylene 2,5-furandicarboxylic) (PEF) or combinations thereof.

According to a further preferred embodiment, the functional insulating layer (2) is a layer of micrometric or nanometric fibre, preferably crossed, or a film layer.

According to another preferred embodiment, the functional insulating layer (2) has a structure of micro or nanoparticles dispersed in any binding means, for example a high viscosity fluid. According to a further alternative preferred embodiment, the functional insulating layer (2) has a structure continuously or discontinuously containing the material of the two preceding preferred embodiments.

Without relating to any theory, in presence of an electric field, namely when the surface of the insulating functional substrate (2) contacts electrically charged (solid or liquid) means, the molecules of the constitutive material, the substrate (2), experience the polarization phenomenon: the molecules of the material are overall oriented in the opposite direction with respect to the electric field in which the substrate material (2) is immersed, namely polarizing with the molecular polarization vector oriented such that the electric dipoles generated have a sign opposite to that of the electric charges present in the contacted means.

Therefore, the functional layer of the medical device object of the invention acts directly on the physiological mechanism underlying the activity of the voltage-dependent ion channels, all due to the functional insulating layer (2) having the characteristic relative dielectric constant, at 1 MHz, from 2.0 to 5.0. Since the medical device, as said, does not release active substances and is not supplied by a battery or any other local or remote energy source (thus has an intrinsic activity), the same is a passive-type device.

According to a further preferred aspect, as illustrated in the experimental part below, the target cutaneous zone for applying the medical device of the invention is an area of the cutis full of sensory receptors (for example mechanorecep-tors or nociceptors).

According to a preferred embodiment, the support layer (1) is an adhesive layer or a buffer layer, preferably an adhesive layer. According to a preferred aspect, in case of adhesive layer, it is selected from an adhesive bandage, preferably a gauze.

In the case where the support layer (1) is not an adhesive layer, i.e., the adhesive layer does not comprise an adhering portion, other techniques known for the skilled person will be employed to maintain the medical device, in particular the functional insulating layer (2), in the correct position contacting the application target cutaneous zone.

According to a preferred aspect, the configuration of the support layer (1) with respect to the functional insulating layer (2) (and possible further layers) is variable. For example, the support layer (1) can partially or totally contour (i.e., surround) the other layers. In this latter case, the support layer (1) can have a frame-like configuration, con-touring the functional insulating layer (2) (and possible further layers).

According to a preferred aspect, the multilayer medical device for cutaneous application of the invention consists of a support layer (1);

a functional insulating layer (2) having a relative dielec-tric constant at 1 MHz, from 2.0 to 5.0. Other features compatible with this two-layer specific configuration are as defined above.

The medical device according to the invention can further comprise an inert material layer (3), preferably of tissue. This layer can be provided to confer or improve the flexural properties of the medical device, in particular of the support layer (1).

The medical device according to the invention can further comprise a flexible layer (4) made of high thermal insulating material, preferably polyamide. Said flexible layer 4 pref-erably contacts the support layer (1).

As experimentally demonstrated in the following examples, the medical device is therapeutically effective in treating nervous system diseases, algodystrophy syndromes, imbalance due to postural alteration, neurological syn-dromes, or combinations thereof. Therefore, according to a further aspect, the invention relates to a medical device for treating a nervous system disease, an algodystrophy syn-drome, an imbalance due to postural alteration, a neurologi-cal syndrome, or combinations thereof.

According to a preferred aspect, the nervous system disease is a neurodegenerative disease. Preferably, said neurodegenerative disease is Parkinson's disease.

According to a preferred aspect, the algodystrophy syn-drome is an algic syndrome. Preferably, said algic syndrome is nociceptive pain.

According to a preferred aspect, the imbalance due to postural alteration is a posture defect induced by trauma/traumas. Preferably, said posture defect induced by trauma/traumas is a proprioceptive response defect.

According to a preferred aspect, the neurological syn-drome is an ataxic syndrome. Preferably, said ataxic syn-drome is a balance chronic disease.

The multilayer medical device of the invention, as described above, can be made by a manufacturing process comprising assembling the layers of interest by adhering the same, preferably by gluing. Subsequently, a pressing of the layers previously adhered to each other can be provided. Subsequently, a cutting step can be provided in order to obtain the medical device of the right size and shape.

Therefore, according to a preferred aspect, a process for manufacturing a multilayer medical device as defined above comprises the steps of:

adhering the layers of interest, preferably by gluing, to obtain a multilayer assembly;

pressing said assembly;

cutting said pressed assembly.

What is reported herein is to be intended for illustrative and non-limiting purposes; therefore, the skilled person will be able to understand that modifications or variations can be made without departing the scope of the present invention.

EXAMPLES

The object of the following examples is to further illus-trate some embodiments of the present invention.

The clinical trials reported below were conducted by applying the two-layer medical device, in which the functional insulating layer had a relative dielectric constant at 1 MHz of 3.5, for therapeutically supporting the following pathologies:

1. Nociceptive pain therapy.
2. Non-pharmacological supportive therapy for improving the movability of the limbs and the static and dynamic postural instability in patients affected by neurovegetative disease such as Parkinson's (Parkinson's Disease or PD).

The results obtained in the clinical field will be detailed below for each of the casuistries dealt with, as well as the application mapping also being object of the present invention will be defined.

1. Clinical Trials Conducted in the Field of Nociceptive Pain Therapy.

The patients were affected by different typologies of nociceptive pain at a local muscular level. In order to clinically evaluate the results, the patient were divided in two groups A and B of 74 patients.

Group A was treated with placebo consisting of a device with a substrate made of common gauze of medical patch and directly applied to the cutis in the target zone according to the typical mappings for treating the nociceptive pain (see the application mappings illustrated below).

The subjective scorecards of the nociceptive pain were prepared according to the scale. The NPRS (or NRS scale) is a 11-point unidimensional scale [15] which evaluate the intensity of the pain in adults [16-17]. The scale is composed by a horizontal line, with a range ranging from 0 to 10, respectively corresponding to "no pain" equal to level 0 and "worst imaginable pain" equal to level 10. The patient indicates the intensity of its own pain verbally or drawing a circle on the number which better describes it.

Therefore, the treated patients expressed the evaluation of the nociceptive pain based on the NRS scale on their own survey before applying the device and 40 minutes after applying the device.

The synthesis results related to Group A (with placebo) and Group B (no placebo) are illustrated below.

Group A with Placebo

Total number of treated patients: 18

Level indication on NRS scale of pre-application perceived pain: 4.78 (average), 1.11 (standard dev.)

Level indication on NRS scale of the pre-application perceived pain: 4.67 (average), 1.08 (standard dev.)

Percentage of patients which do not found any variation on NRS scale: 88.9%

Maximum found variation on NRS scale: 1

The synthesis results related to Group B (no placebo) and Group B (no placebo) are illustrated below.

Group B No Placebo:

Total number of treated patients: 59

Level indication on NRS scale of pre-application perceived pain: 4.97 (average), 1.54 (standard dev.)

Level indication on NRS scale of pre-application perceived pain: 3.87 (average), 1.93 (standard dev.)

Percentage of the treated patients which do not find any variation on NRS scale: 33.9%

Maximum found variation on NRS scale: 4

Application mappings of the device:

Applying in the pain point (low back pain, neck pain, back pain, various muscle contractures).

2. Clinical Trials Conducted for the Non-Pharmacological Supportive Therapy for Improving the Movability of the Limbs and the Static and Dynamic Postural Instability in Patients Affected by Neurovegetative Diseases Such as Parkinson's (Parkinson's Disease or PD).

2.1 Measures of the H Reflex Parameter on Patients with Spasticity

The vibration tonic reflex or Hoffman reflex (also called spinal reflex H or H-reflex) consists of a prolonged contraction of a muscle subjected to (electric or vibrational) stimulus. It is an electrophysiological-type test which employs both stimulating electrodes and recording electrodes. The stimulating electrodes are positioned near the nerve; a rectangular impulse (1 ms) which activates the nerve fibres with intensity of the electric stimulus being firstly low, then increased, is emitted. Increasing the intensity of the stimulus activates the surface mechanoreceptors, those of the tendons and especially those of the muscle spindles where an action potential transmitting the signal in afference is generated. The discharges of the muscle spindle are sent to the spinal cord through the afferent nerve fibres, where they activate the poli-synaptic reflected arcs, causing the contraction of the muscle, generating as a return an electric signal read by the recording electrodes.

The tonic vibration reflex is evocated generally positioning a vibration-emitting probe on the tendon of a muscle in the order of 30-100 Hz.

It is known that applying focal vibrations or FV with frequency between 100 and 200 Hz on the target muscle has a substantial effect on the H Reflex index which is reduced [18].

It is known that reducing H-Reflex obtained by applying FV in patients affected by PD leads to the resulting improving on spasticity since the external vibrational stress is able to activate an important pre-synaptic inhibition. Furthermore, applying the focal vibrations as a reduction of the H reflex is considered underlying the improvement of the posture and the balance in PD patients [18] based on the theory assuming the afferent stimulus along the primary fibres "Ia" and "Ib" and secondary fibres II, being afferent to the cortex improving the proprioceptive information [18]. Since these fibres are in the proprioceptors (i.e., muscle spindles, Golgi, and more superficially the Pacini and Messner mechanoreceptors), they all consist of mechano-dependent axons able to depolarize and send action potential trains.

H-Reflex Test on PD Patients with and without Device Applied 8 patients affected by spasticity were examined with H-Reflex test.

Test Protocol:

The patient is placed immobile on the couch ("T0" state) and the stimulating electrodes are applied to the tibial and popliteal fossa and two other recording electrodes on the soleus for measuring the reflex H.

Trains of electric impulses of a few mA (1 impulse each 2 seconds) with increasing width are imposed. Upon increasing of the stimulus current intensity, the reflex H increases up to a maximum and then decreases. Because of the stretch reflex the motoneurons alpha are activated.

The H index is measured with patient:

T0: static and without device applied;

T1: static with device applied on the soleus, measures conducted 3 minutes after the application T2: static, with device applied and with FV applied at 100 hertz on the target muscle (soleus).

The ratio between the measured index H and the parameter M equal to the maximum value of H is a measure of the quantity of motoneurons alpha activated for stimulating the target muscle. In patients with spasticity, H/M max values equal to 0.8 generally occur.

Test Results on Patients Treated with Device

The device is applied at the soleus measuring the parameter H 3 minutes after the application.

In 75% of patients, a percentage variation from T0 to T1 with lowering of the parameter H of 90% on average was recorded.

The reduction is due to the presynaptic inhibition (inhibition of the afferent signal of the motoneurons alpha). Applying the device to a static patient produces a remarkably reduced reflex H, index of the inhibition of the motoneurons alpha involved in the muscle tone.

In 85% of patients, a reduction of the value H from T0 to T2 of 95% was recorded.

Interpretation of the Results

The device applied on the target point of the soleus inhibits and adjusts the action potentials of the epidermis and cutaneous mechanoreceptors, mainly, intervening on the repolarization of the afferent neuronal membranes and reducing the spastic phenomena.

The device naturally also acts on patient T0 because of the muscle tone. It performs its inhibiting action on the afferent signals of the motoneurons alpha in patients T1 and amplifies its own effect for reducing the spasticity in patients T2.

2.2 Gait Analysis Surveys on PD Patients with BTS G-Walk

Gait Analysis (GA) or instrumental analysis of the gait is the systematic study of the human movement being performed employing accelerometers able to measure specific parameters of the movement, on the basis of the interpretation of which the skilled person is able to infer the general peculiarities of the mechanics of the body in patients affected by PD as well as to quantitatively evaluate improving or worsening of the motor performance of such patients depending on specific therapies or simply the evolution of the motor diseases over the progression time of the neurovegetative disease.

Test Protocol and Measure Parameters

An accelerometer is positioned by means of a belt in the proximity of S1. Preferably, the check belt should directly contact the epidermis of the patient. The accelerometer wirelessly sends the acquired data to the processing unit.

The patient deambulates without footwears along a preset rectilinear trajectory and goes back to the starting point. The length of the overall rectilinear path should be at least 10 meters.

Parameters for Analysing the Gait of PD Patients by Gait Analysis

For patients affected by PD, during the walking test, there is an evaluation mainly of:

Linear walking

180° turning for inverting the direction

Stop-and-go phase

The following parameters measure during the test with BTS G-Walk for PD subjects are generally assumed to be relevant:

Duration of the test [sec]

Risk of falling [at risk/not at risk]

Front-rear acceleration (standing and seating) [metres/sec]

Flexion-extension of the stem—Duration of standing

Flexion peak [degrees]

Flexion width [in degrees]

Flexion-extension of the stem—Duration of seating:

Flexion peak [degrees]

Extension peak [degrees]

Extension width [degrees]

Intermediate turning [sec]

Final turning [sec]

Table 1 reports the values of the characteristic parameters observed for:

S=14 healthy subjects

PD=14 subjects affected by Parkinson's;

In the experimental conditions:

T0=device unapplied

T1=device applied and test performed 45 minutes after the application

TABLE 1

| Gait Analysis BTS G-Walk measured parameters | S | T0 | T1 | Improvement % |
|---|---|---|---|---|
| Duration of the test [sec] | 9.49 | 18.42 | 16.49 | 10.51% |
| Risk of falling* percentage | — | 93.0% | 46.7% | 46.3% |
| Front-rear acceleration (stand) [m/sec2] | 5.05 | 2.21 | 2.97 | 34.04% |
| Front-rear acceleration (seated) [m/sec2] | 5.07 | 3.03 | 3.80 | 25.27% |
| Flexion-extension of the stem - Duration of standing: flexion peak [degrees] | 31.36 | 25.78 | 30.83 | 19.60% |
| Flexion-extension of the stem - Duration of standing: flexion width [degrees] | 32.69 | 24.63 | 30.59 | 24.20% |
| Flexion-extension of the stem - Duration of seating: flexion peak [degrees] | 32.77 | 27.08 | 30.81 | 13.76% |
| Flexion-extension of the stem - Duration of seating: extension peak [degrees] | 8.76 | 6.90 | 9.21 | 33.43% |
| Flexion-extension of the stem - Duration of seating: extension width [degrees] | 20.54 | 13.13 | 19.35 | 47.36% |
| Intermediate turning [sec] | 1.64 | 3.86 | 3.02 | 21.96% |
| Final turning [sec] | 1.81 | 3.65 | 3.00 | 18.01% |

*Calculated by parameters measured by Gait Analysis by G-Walk.

Application Mapping
  2 devices: bilateral insertion of the triceps surae, 1 device
     in seat C7 (prominent cervical vertebra)

The invention claimed is:

1. A multilayer medical device for cutaneous application, said multilayer medical device being a passive type-device and comprising:
  a support layer;
  a functional insulating layer having a relative dielectric constant, at 1 MHz, from 2.0 to 5.0.

2. The multilayer medical device of claim 1 wherein said multilayer medical device is not supplied by any external energy source.

3. The multilayer medical device of claim 1, wherein the functional insulating layer has a dissipation factor, at 1 MHz, lower than or equal to 0.05.

4. The multilayer medical device of claim 1, wherein the functional insulating layer has a thermal conductivity W/(K*m) lower than or equal to 0.29.

5. The multilayer medical device of claim 1, wherein the functional insulating layer has a surface comprised between 2 and 12 cm$^2$.

6. The multilayer medical device of claim 1, wherein the functional insulating layer is a polymeric layer.

7. The multilayer medical device of claim 6, wherein the polymeric layer comprises a polyester.

8. The multilayer medical device of claim 1, wherein the support layer is an adhesive layer or a buffer layer.

9. The multilayer medical device of claim 7, wherein the adhesive layer is selected from an adhesive bandage and the buffer layer is a gauze.

10. The multilayer medical device of claim 1, further comprising an inert material layer.

11. The multilayer medical device of claim 1, further comprising a flexible layer of high thermal insulating material.

12. The multilayer medical device of claim 1, for treating a nervous system disease.

13. The multilayer medical device of claim 12, wherein the nervous system disease is a neurodegenerative disease.

14. The multilayer medical device of claim 13, wherein the neurodegenerative disease is Parkinson's disease.

15. The multilayer medical device of claim 1, for treating algodystrophy syndrome, wherein the algodystrophy syndrome is an algic syndrome.

16. The multilayer medical device of claim 15, wherein the algic syndrome is nociceptive pain.

17. The multilayer medical device of claim 1, for treating an imbalance due to postural alteration, wherein the imbalance due to postural alteration is a posture defect induced by trauma/traumas.

18. The multilayer medical device of claim 17, wherein the posture defect induced by trauma/traumas is a proprioceptive response defect.

19. The multilayer medical device of claim 1, for treating a neurological syndrome, wherein the neurological syndrome is an ataxic syndrome.

20. The multilayer medical device of claim 19, wherein the ataxic syndrome is a balance chronic disease.

21. The multilayer medical device of claim 1 is configured for treating a combination of two or more of the following diseases: an algodystrophy syndrome, an imbalance due to postural alteration, and a neurological syndrome.

22. The multilayer medical device of claim 1, wherein said multilayer medical device is not configured to release substances.

*   *   *   *   *